United States Patent
Yoshino et al.

(10) Patent No.: US 9,102,141 B2
(45) Date of Patent: Aug. 11, 2015

(54) CAPACITIVE LOAD DRIVING CIRCUIT, INK JET PRINTER, AND FLUID EJECTING APPARATUS

(75) Inventors: Hiroyuki Yoshino, Matsumoto (JP); Atsushi Oshima, Shiojiri (JP); Kunio Tabata, Shiojiri (JP); Shinichi Miyazaki, Suwa (JP); Noritaka Ide, Shiojiri (JP)

(73) Assignee: Seiko Epson Corporation, Tokyo (JP)

( * ) Notice: Subject to any disclaimer, the term of this patent is extended or adjusted under 35 U.S.C. 154(b) by 520 days.

(21) Appl. No.: 13/075,429

(22) Filed: Mar. 30, 2011

(65) Prior Publication Data
US 2011/0242172 A1 Oct. 6, 2011

(30) Foreign Application Priority Data

Mar. 30, 2010 (JP) .................................. 2010-077496

(51) Int. Cl.
*B41J 29/38* (2006.01)
*A61B 17/3203* (2006.01)
*B41J 2/015* (2006.01)
(Continued)

(52) U.S. Cl.
CPC ........... *B41J 2/0455* (2013.01); *A61B 17/3203* (2013.01); *B41J 2/04541* (2013.01); *B41J 2/04581* (2013.01); *B41J 2/04588* (2013.01); *B41J 2/04593* (2013.01); *B41J 2/04596* (2013.01)

(58) Field of Classification Search
USPC ............ 347/5, 10, 20, 54, 68; 330/10, 207 A, 330/251, 207; 332/109
See application file for complete search history.

(56) References Cited

U.S. PATENT DOCUMENTS

| | | | |
|---|---|---|---|
| 4,144,502 A | * | 3/1979 | Ikeda .......................... 330/207 A |
| 5,600,234 A | * | 2/1997 | Hastings et al. ............... 323/282 |

(Continued)

FOREIGN PATENT DOCUMENTS

| | | | | |
|---|---|---|---|---|
| JP | h03 f | * | 9/1998 | .............. H03F 3/217 |
| JP | 2000307359 A | * | 11/2000 | .............. H03F 3/217 |

(Continued)

OTHER PUBLICATIONS

Sedra, Adel S., and Kenneth Carless Smith (Microelectronic circuits. New York: Holt, Rinehart and Winston, 1982. Print pp. 522-252, 571-573.*

(Continued)

*Primary Examiner* — Jannelle M Lebron
*Assistant Examiner* — Jeremy Bishop
(74) *Attorney, Agent, or Firm* — Workman Nydegger

(57) ABSTRACT

A capacitive load driving circuit includes: a drive waveform signal generator that generates a drive waveform signal; a subtractor that outputs a differential signal between the drive waveform signal and a feedback signal; a modulator that pulse-modulates the differential signal and outputs a modulated signal; a digital power amplifier that amplifies the power of the modulated signal and outputs a power-amplified modulated signal; a smoothing filter that smoothes the power-amplified modulated signal, and outputs a drive signal of the capacitive load; a compensator that causes a phase to precede the drive signal; and an attenuator that attenuates signal amplitude in a band at least including a modulation frequency of the modulated signal. A signal output from a connecting point between the inductor and the wire is made to pass through the compensator and the attenuator and is then used as a feedback signal to the subtractor.

8 Claims, 13 Drawing Sheets

(51) Int. Cl.
*B41J 2/04* (2006.01)
*B41J 2/045* (2006.01)
*H03F 3/38* (2006.01)
*H03F 3/217* (2006.01)
*H03F 1/04* (2006.01)
*H03F 1/34* (2006.01)
*H03K 7/08* (2006.01)

(56) References Cited

U.S. PATENT DOCUMENTS

| | | | |
|---|---|---|---|
| 5,838,193 A * | 11/1998 | Myers et al. | 330/10 |
| 5,963,443 A * | 10/1999 | Mihara | 363/134 |
| 6,286,922 B1 * | 9/2001 | Kondou | 347/10 |
| 6,897,725 B2 * | 5/2005 | Honda | 330/207 A |
| 6,952,131 B2 * | 10/2005 | Jeong et al. | 330/10 |
| 7,084,799 B1 * | 8/2006 | Butler | 341/143 |
| 7,151,404 B2 * | 12/2006 | Lee et al. | 330/10 |
| 7,183,840 B2 * | 2/2007 | Maejima | 330/10 |
| 7,295,062 B2 * | 11/2007 | Fenger | 330/10 |
| 7,400,191 B2 * | 7/2008 | Rodriguez | 330/10 |
| 7,461,281 B2 * | 12/2008 | Miyazaki | 713/323 |
| 7,571,989 B2 * | 8/2009 | Ishizaki | 347/57 |
| 7,642,877 B2 * | 1/2010 | Clara et al. | 332/109 |
| 7,683,708 B2 * | 3/2010 | Koch | 330/10 |
| 7,746,127 B2 * | 6/2010 | Miyazaki et al. | 327/112 |
| 7,850,265 B2 * | 12/2010 | Ishizaki | 347/9 |
| 8,013,678 B2 * | 9/2011 | Nielsen et al. | 330/251 |
| 8,256,858 B2 * | 9/2012 | Oshima et al. | 347/10 |
| 8,262,183 B2 * | 9/2012 | Oshima et al. | 347/10 |
| 2005/0162223 A1 | 7/2005 | Maejima | |
| 2005/0231179 A1 | 10/2005 | Ishizaki | |
| 2005/0248894 A1 * | 11/2005 | Bliley et al. | 361/92 |
| 2006/0245517 A1 * | 11/2006 | Ikedo et al. | 375/297 |
| 2007/0079710 A1 | 4/2007 | Ishizaki | |
| 2007/0124620 A1 | 5/2007 | Miyazaki | |
| 2007/0165074 A1 | 7/2007 | Ishizaki | |
| 2007/0247219 A1 | 10/2007 | Rodriguez | |
| 2008/0218545 A1 | 9/2008 | Oshima et al. | |
| 2009/0140780 A1 | 6/2009 | Miyazaki et al. | |
| 2009/0160891 A1 | 6/2009 | Ishizaki | |
| 2009/0167798 A1 | 7/2009 | Ide et al. | |
| 2011/0109674 A1 | 5/2011 | Oshima | |

FOREIGN PATENT DOCUMENTS

| | | |
|---|---|---|
| JP | 2005-329710 | 12/2005 |
| JP | 2007-096364 | 4/2007 |
| JP | 2007-168172 | 7/2007 |
| JP | 2007-190708 | 8/2007 |
| JP | 2008-087467 | 4/2008 |
| JP | 2009-131990 | 6/2009 |
| JP | 2009-153272 | 7/2009 |

OTHER PUBLICATIONS

European Search Report for European Patent Application No. 11159971.8 dated Jan. 22, 2014.

* cited by examiner

CAPACITIVE LOAD DRIVING CIRCUIT, INK JET PRINTER, AND FLUID EJECTING APPARATUS

CROSS REFERENCE TO RELATED APPLICATIONS

This application claims the benefit of Japanese Application No. 2010-077496 filed on Mar. 30, 2010, which application is incorporated by reference in its entirety.

BACKGROUND

1. Technical Field

Embodiments of the present invention relate to a capacitive load driving circuit that supplies a drive signal to a capacitive load such as a piezoelectric element so as to drive the capacitive load. More particularly, embodiments of the invention relate to an ink jet printer that includes an actuator as a capacitive load and that performs a printing operation by supplying a drive signal to the actuator so as to eject ink or to a fluid ejecting apparatus that includes an actuator such as a capacitive load connected to a diaphragm and that supplies a drive signal to the actuator so as to eject fluid.

2. Related Art

For example, when a drive waveform signal having a predetermined voltage waveform is amplified by a digital power amplifier and is used as a drive signal of an actuator, which is a capacitive load, the drive waveform signal is pulse-modulated into a modulated signal by a modulator, the modulated signal is amplified in power into a power-amplified modulated signal by the digital power amplifier, and the power-amplified modulated signal is smoothed into a drive signal by a smoothing filter.

When the waveform of the drive signal is important, a feedback signal can be generated from the drive signal. The feedback signal is phase shifted from the drive signal and may precede the drive signal in phase. A differential value between the feedback signal and the drive waveform signal obtained from a subtractor may be input to the modulator. For example, in JP-A-2007-96364, by inserting a phase-preceding compensator into a feedback circuit of a drive signal, an attempt is made to compensate for the waveform of the drive signal without inserting a dumping resistor before or after a smoothing filter. The pulse-modulated frequency in the modulator is referred to as a modulation frequency or a carrier frequency.

When an actuator as a capacitive load is separated from a digital power amplifier, a wire in addition to a substrate interconnection is necessary between the actuator and the digital power amplifier. In this case, it is not realistic that the drive signal actually supplied to the actuator be fed back, because an individual wire is necessary and the like. Accordingly, for example, an inductor is disposed at an output terminal of the digital power amplifier and a signal at a connecting point between the inductor and the wire is fed back. However, when the input signal to the wire is fed back, signal amplitude in a modulation frequency band exceeding an operating range of the subtractor or the modulator may remain in a feedback signal when only the phase-preceding compensator is inserted into the feedback circuit. In this case, there is a problem because it is not possible to satisfactorily compensate for the drive signal.

SUMMARY

Embodiments of the invention provide a capacitive load driving circuit, an ink jet printer, and a fluid ejecting apparatus. Embodiments of the invention can prevent signal amplitude in a modulation frequency band exceeding an operating range of a subtractor or a modulator from remaining in a feedback signal.

According to an embodiment of the invention, a capacitive load driving circuit is provided. The capacitive load driving circuit includes: a drive waveform signal generator that generates a drive waveform signal; a subtractor that outputs a differential signal between the drive waveform signal and a feedback signal; a modulator that pulse-modulates the differential signal and outputs a modulated signal; a digital power amplifier that amplifies the power of the modulated signal and outputs a power-amplified modulated signal; a smoothing filter that is constructed by connecting an inductor and a capacitive load with a wire, smoothes the power-amplified modulated signal, and outputs a drive signal of the capacitive load; a compensator that causes a phase of the feedback signal to precede the phase of the drive signal; and an attenuator that attenuates signal amplitude in a band at least including a modulation frequency of the modulated signal. In one embodiment, a signal output from a connecting point between the inductor and the wire is made to pass through the compensator and the attenuator and is then used as the feedback signal to the subtractor.

According to an embodiment of the capacitive load driving circuit, for example, when a wire is necessarily disposed between the capacitive load of the actuator and the digital power amplifier, the inductor and the capacitive load are connected with the wire to form a smoothing filter and the signal output from the connecting point between the inductor and the wire is made to pass through the compensator and the attenuator and is then used as the feedback signal to the subtractor. Accordingly, it is possible to attenuate the signal amplitude in a modulation frequency band of the feedback signal by the use of the attenuator while removing the resonance peak from a transfer function characteristic of the drive signal. As a result, it is possible to prevent the signal amplitude in the modulation frequency band exceeding the operating range of the subtractor or the modulator from remaining in the feedback signal while compensating for the waveform of the drive signal, and to guarantee the precision of the drive signal.

In an embodiment of the capacitive load driving circuit, the compensator may include a capacitor and a resistor, and the attenuator may be configured to include the resistor of the compensator. It is possible to simplify the circuit configuration and to set the attenuation characteristic of the attenuator to various values.

In an embodiment of the capacitive load driving circuit, the attenuator may attenuate the signal amplitude so as not to exceed an allowable operating range of at least one of the subtractor and the modulator. It is possible to more satisfactorily prevent the signal amplitude in the modulation frequency band exceeding the operating range of the subtractor or the modulator from remaining in the feedback signal.

In an embodiment of the capacitive load driving circuit, the attenuator may have a phase-lag characteristic. It is possible to remove the distortion of the feedback signal by the use of an integration function based on the phase-lag characteristic.

In an embodiment of the capacitive load driving circuit, the attenuator may include one or more resistors. It is possible to remove the distortion of the feedback signal with a simpler configuration.

In an embodiment of the capacitive load driving circuit, the attenuator may include a plurality of attenuators. It is possible to more satisfactorily remove the distortion of the feedback signal.

According to another embodiment of the invention, an ink jet printer is provided having a plurality of actuators as a capacitive load in an ink jet head, applying a drive signal to the actuators so as to reduce a volume of a pressure chamber and to eject ink in the pressure chamber, and performing a printing operation on a printing medium with the ejected ink. The ink jet printer includes: a drive waveform signal generator that generates a drive waveform signal; a subtractor that outputs a differential signal between the drive waveform signal and a feedback signal; a modulator that modulates the differential signal and outputs a modulated signal; a digital power amplifier that amplifies the power of the modulated signal and outputs a power-amplified modulated signal; a smoothing filter that is constructed by connecting an inductor and the actuators with a wire, smoothes the power-amplified modulated signal, and outputs the drive signal; a compensator that causes a phase to precede the drive signal; and an attenuator that attenuates signal amplitude in a band at least including a carrier frequency of the modulated signal singly or in combination with the compensator. In this embodiment, a signal output from a connecting point between the inductor and the wire is made to pass through the compensator and the attenuator and is then used as the feedback signal to the subtractor.

According to this embodiment of the ink jet printer, when the drive signal is applied to the actuator as a capacitive load, the volume of the pressure chamber of the ink jet head is reduced to eject ink in the pressure chamber and a printing operation is performed on a printing medium with the ejected ink. At this time, the inductor and the actuator as the capacitive load are connected with the wire to form the smoothing filter and the signal output from the connecting point between the inductor and the wire is made to pass through the compensator and the attenuator and is then used as a feedback signal to the subtractor. Accordingly, it is possible to attenuate the signal amplitude in a modulation frequency band of the feedback signal by the use of the attenuator while removing the resonance peak from a transfer function characteristic of the drive signal. As a result, it is possible to prevent the signal amplitude in the modulation frequency band exceeding the operating range of the subtractor or the modulator from remaining in the feedback signal while compensating for the waveform of the drive signal, and to guarantee the precision of the drive signal, thereby performing a printing operation with higher precision.

According to still another embodiment of the invention, there is provided a fluid ejecting apparatus having a plurality of actuators as a capacitive load connected to a diaphragm and applying a drive signal to the actuators so as to reduce a volume of a fluid chamber by means of the diaphragm and to eject fluid in the fluid chamber. The fluid ejecting apparatus includes: a drive waveform signal generator that generates a drive waveform signal; a subtractor that outputs a differential signal between the drive waveform signal and a feedback signal; a modulator that modulates the differential signal and outputs a modulated signal; a digital power amplifier that amplifies the power of the modulated signal and outputs a power-amplified modulated signal; a smoothing filter that is constructed by connecting an inductor and the actuators with a wire, smoothes the power-amplified modulated signal, and outputs the drive signal; a compensator that causes a phase to precede the drive signal; and an attenuator that attenuates signal amplitude in a band at least including a carrier frequency of the modulated signal singly or in combination with the compensator. Here, a signal output from a connecting point between the inductor and the wire is made to pass through the compensator and the attenuator and is then used as the feedback signal to the subtractor.

According to this embodiment of the fluid ejecting apparatus, when the drive signal is applied to the actuator as a capacitive load, the volume of the fluid chamber is reduced by means of the diaphragm to eject fluid in the fluid chamber. At this time, the inductor and the actuator as the capacitive load are connected with the wire to form the smoothing filter and the signal output from the connecting point between the inductor and the wire is made to pass through the compensator and the attenuator and is then used as the feedback signal to the subtractor. Accordingly, it is possible to attenuate the signal amplitude in a modulation frequency band of the feedback signal by the use of the attenuator while removing the resonance peak from a transfer function characteristic of the drive signal. As a result, it is possible to prevent the signal amplitude in the modulation frequency band exceeding the operating range of the subtractor or the modulator from remaining in the feedback signal while compensating for the waveform of the drive signal, and to guarantee the precision of the drive signal, thereby ejecting the fluid with higher precision.

BRIEF DESCRIPTION OF THE DRAWINGS

Embodiments of the invention are described with reference to the accompanying drawings, where like numbers reference like elements.

FIG. 9A is a block diagram of the feedback circuit and FIG. 9B is a diagram illustrating a frequency characteristic of the feedback circuit.

FIG. 12A is a block diagram of the feedback circuit and FIG. 12B is a diagram illustrating a frequency characteristic of the feedback circuit.

3, where FIG. 17A is a block diagram of the feedback circuit and FIG. 17B is a diagram illustrating a frequency characteristic of the feedback circuit.

FIG. 17A is a block diagram of the feedback circuit and FIG. 17B is a diagram illustrating a frequency characteristic of the feedback circuit.

FIG. 20A is a block diagram of the feedback circuit and FIG. 20B is a diagram illustrating a frequency characteristic of the feedback circuit.

DETAILED DESCRIPTION

Hereinafter, a capacitive load driving circuit according to a first embodiment of the invention which is applied to an ink jet printer will be described.

Figure 1:
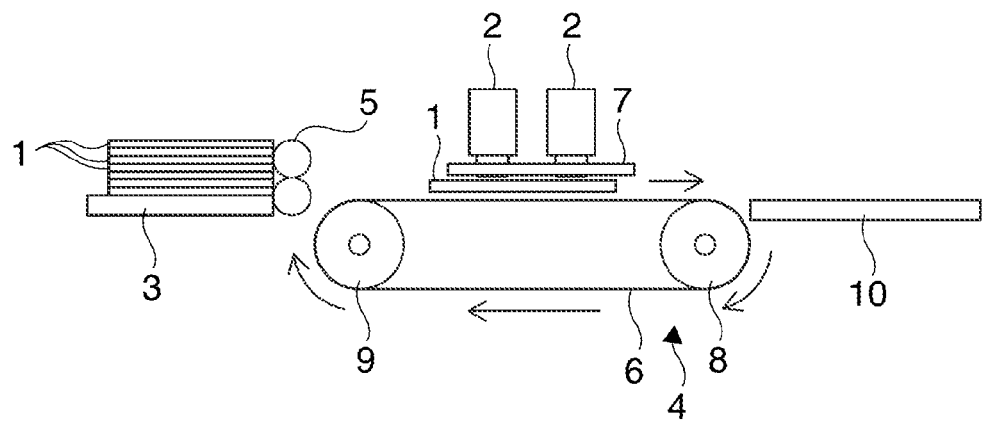
FIG. 1 is a front view schematically illustrating a configuration of an ink jet printer employing a capacitive load driving circuit according to a first embodiment of the invention.

FIG. 1 is a diagram schematically illustrating the configuration of an ink jet printer according to this embodiment. The ink jet printer shown in FIG. 1 is a line head type ink jet printer in which a printing medium 1 is transported in the arrow direction from the left to the right in the drawing and is subjected to a printing operation in a print area of a transport line.

In FIG. 1, reference numeral 2 represents plural ink jet heads disposed above the transport line of the printing medium 1. The ink jet heads are arranged along a direction intersecting the printing medium transport direction so as to form two lines in the printing medium transport direction. The ink jet heads 2 are fixed to a head fixing plate 7. Plural nozzles are formed in the bottom surface of each ink jet head 2 and thus the bottom surface of each ink jet head 2 is called a nozzle surface.

Figure 2:
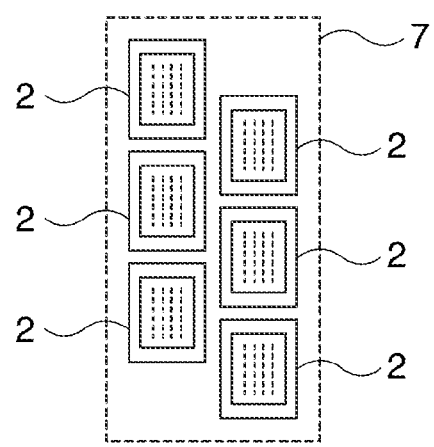
FIG. 2 is a plan view illustrating an example of the arrangement of an ink jet head used in the ink jet printer shown in FIG. 1.

As shown in FIG. 2, the nozzles are arranged in a line in the direction intersecting the printing medium transport direction for each color of ink to be ejected, and thus the line is called a nozzle line or the line direction is called a nozzle line direction. The nozzle lines of the ink jet heads 2 arranged in the direction intersecting the printing medium transport direction form a line head covering the entire width in the direction intersecting the transport direction of the printing medium 1.

The ink jet heads 2 are supplied with four colors of ink (yellow (Y), magenta (M), cyan (C), and black (K)) from ink tanks not shown via ink supply tubes. The ink is simultaneously ejected to a predetermined position by a necessary amount from the nozzles formed in the ink jet heads 2, each nozzle thereby forming a fine dot on the printing medium 1 and the nozzles thereby forming a line of fine dots. By performing this operation for each color, a one-pass printing operation can be performed by passing the printing medium 1 transported by a transport unit 4 only once.

In this embodiment, a piezoelectric method is used as a method of ejecting ink from the nozzles of the ink jet heads 2. In the piezoelectric method, when a drive signal is applied to a piezoelectric element, which is an example of an actuator, a vibration membrane in a pressure chamber is displaced to vary the volume of the pressure chamber and ink in the pressure chamber is ejected from the nozzles by means of the variation in pressure resulting therefrom. The amount of ink to be ejected can be adjusted by adjusting the crest value of the drive signal or the voltage change slope. Embodiments of the invention can be similarly applied to an ink ejecting method other than the piezoelectric method.

A transport unit 4 transporting the printing medium 1 in a transport direction is disposed below the ink jet heads 2. In the transport unit 4, a transport belt 6 is wound on a driving roller 8 and a driven roller 9 and an electric motor not shown is connected to the driving roller 8. A suction unit (not shown) suctioning the printing medium 1 onto the surface of the transport belt 6 is disposed on the inside of the transport unit 4. Examples of the suction unit include a vacuum suction unit suctioning the printing medium 1 onto the transport belt 6 using a negative pressure and an electrostatic suction unit suctioning the printing medium 1 onto the transport belt 6 using an electrostatic force. Accordingly, when a sheet of the printing medium 1 is fed to the transport belt 6 from a sheet feed unit 3 by a feed roller 5 and the driving roller 8 is rotationally driven by the electric motor, the transport belt 6 rotates in the printing medium transport direction and the printing medium 1 is suctioned onto the transport belt 6 by the suction unit and the printing medium 1 is then transported on the transport belt 6.

In the course of transporting the printing medium 1, ink is ejected from the ink jet heads 2 to perform a printing operation. The printing medium 1 having been subjected to the printing operation is discharged to a sheet discharge unit 10 downstream in the transport direction. A print reference signal output unit including, for example, a linear encoder is disposed in the transport unit 4, and ink of a predetermined color is ejected to a predetermined position on the printing medium 1 to form a dot (or dots) by outputting a drive signal to the actuator from a driver (to be described later) on the basis of a pulse signal corresponding to a requested resolution and being output from the print reference signal output unit, whereby a predetermined image is drawn on the printing medium 1 by the use of the dots.

Figure 3:
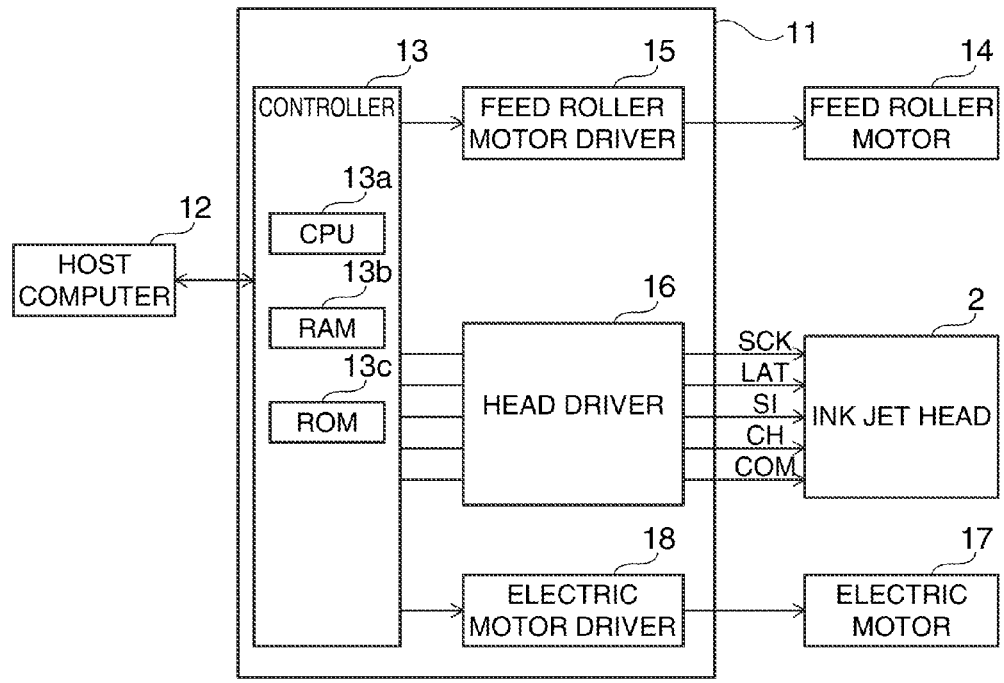
FIG. 3 is a block diagram illustrating the configuration of a control unit of the ink jet printer shown in FIG. 1.

The ink jet printer according to this embodiment is provided with a control unit 11 controlling the ink jet printer. An example of the configuration of the control unit 11 is shown in FIG. 3. First, print data input from a host computer 12 is read. The control unit 11 includes a controller 13 constructed by a computer system performing various processes such as a printing process on the basis of the print data, a feed roller motor driver 15 controlling the driving of a feed roller motor 14 connected to the feed roller 5, a head driver 16 controlling the driving of the ink jet heads 2, and an electric motor driver 18 controlling the driving of the electric motor 17 connected to the driving roller 8.

The controller 13 includes a CPU (Central Processing Unit) 13a, a RAM (Random Access Memory) 13b, and a ROM (Read Only Memory) 13c. When the CPU 13a performs various processes such as a printing process, the RAM 13b temporarily stores the input print data or various data used to perform the print data printing process or temporarily develops programs of the printing process and the like. The ROM 13c includes a nonvolatile semiconductor memory storing a control program to be executed by the CPU 13a. When the controller 13 receives print data (image data) from the host computer 12, the CPU 13a performs a predetermined process on the print data and calculates nozzle selection data (drive pulse selection data) indicating which nozzles are to eject ink and/or what amount of ink is to be ejected. The controller outputs a control signal and a drive signal to the feed roller motor driver 15, the head driver 16, and the electric motor driver 18 on the basis of the print data, the drive pulse selection data, and input data from various sensors. In response to the control signal or the drive signal, the feed roller motor 14, the electric motor 17, and the actuators in the ink jet heads 2 work, whereby the processes of feeding, transporting, and discharging the printing medium 1 and the process of performing a printing process on the printing medium 1 are carried out. The elements of the controller 13 are electrically connected to each other via a bus not shown.

Figure 4:
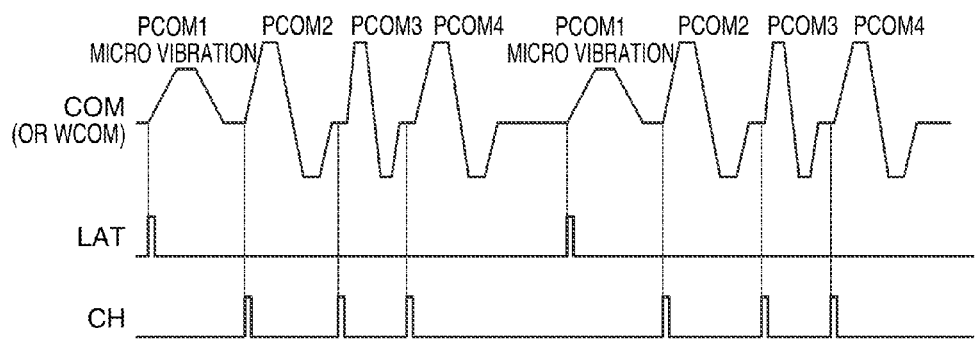
FIG. 4 is a diagram illustrating a drive signal of an actuator which is a capacitive load.

FIG. 4 shows an example of a drive signal COM being supplied to the ink jet heads 2 from the head driver 16 of the control unit 11 and being used to drive the actuators, which may include piezoelectric elements. In this embodiment, the drive signal is a signal in which a voltage varies about a middle voltage. The drive signal COM is formed by connecting drive pulses PCOM as a unit drive signal used to drive the actuators to eject ink in a time series. At the rising edge of each drive pulse PCOM, the volume of the pressure chamber communicating with the nozzles is enlarged to intrude the ink therein. At the falling edge of each drive pulse PCOM, the volume of the pressure chamber is reduced to extrude the ink therefrom. By extruding the ink, the ink is ejected from the nozzles.

By variably changing the voltage change slope or the crest value of the drive pulse PCOM, which may have a trapezoidal voltage waveform, an intrusion amount or intrusion rate of ink or an extrusion amount or an extrusion rate of ink can be changed and the amount of ink to be ejected can be accordingly changed. In this manner, different sizes of dots can be formed.

Therefore, even when multiple drive pulses PCOM are connected in a time series, various sizes of dots are obtained by selecting a single drive pulse PCOM therefrom and supplying the selected drive pulse to the actuators 19 or selecting multiple drive pulses PCOM and supplying the selected drive pulses to the actuators 19 and ejecting the ink multiple times. That is, when multiple ink droplets land onto the same position before the ink is dried, it is the same as actually ejecting a large size ink droplet. Thus, the size of a dot can be enlarged. By combining such techniques, multi gray scales can be realized. The drive pulse PCOM1 on the leftmost side in FIG. 4 only intrudes the ink therein but does not extrude the ink. This is called micro vibration, which is used not to eject ink but to suppress or prevent thickening of the ink at or in the nozzles or in the pressure chamber.

In addition to the drive signal COM, a drive pulse selection data SI, a latch signal LAT, a channel signal CH, and a clock signal SCK used to transmit the drive pulse selection data SI as a serial signal to the ink jet heads 2 are input as the control signal to the ink jet heads 2 from the control unit shown in FIG. 3. The drive pulse selection data SI is data indicating what drive pulse PCOM to select from the drive pulses PCOM on the basis of the print data. The latch signal LAT and the channel signal CH connect the drive signal COM to the actuators of the ink jet heads 2 on the basis of the drive pulse selection data SI after inputting the nozzle selection data to all the nozzles. Hereinafter, the minimum unit of the drive signal for driving the actuators 19 is referred to as the drive pulse PCOM and the signal in which the drive pulses PCOM are connected in a time series is referred to as the drive signal COM. That is, a series of drive signals COM is output in response to the latch signal LAT and the drive pulse PCOM is output for each channel signal CH.

Figure 5:
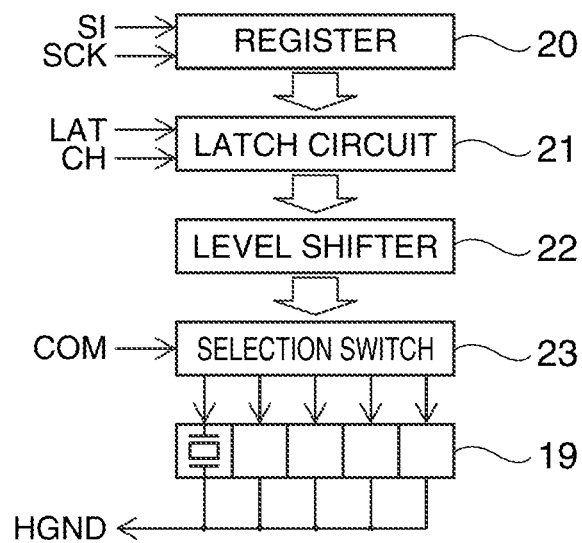
FIG. 5 is a block diagram illustrating a switching controller.

FIG. 5 shows the specific configuration of a switching controller built in the ink jet heads 2 so as to supply the drive signal COM (drive pulses PCOM) to the actuators 19. The switching controller includes a register 20, a latch circuit 21 temporarily storing data of the register 20, and a level shifter 22 connecting the drive signal COM (drive pulses PCOM) to the actuators 19 including a piezoelectric element by converting the level of the output of the latch circuit 21 and supplying the converted signal to a selection switch 23. The register 20 stores the drive pulse selection data SI for selecting the actuator 19 of a piezoelectric element corresponding to the nozzle ejecting the ink.

The level shifter 22 converts the output of the latch circuit into a voltage level capable of turning the selection switch 23 on or off. This is because the drive signal COM (drive pulses PCOM) is higher than the output voltage of the latch circuit 21 and thus the operation voltage range of the selection switch 23 is set to be high. Therefore, the actuators 19 which the selection switch 23 turn on by the level shifter 22 are connected to the drive signal COM (drive pulses PCOM) at a predetermined connection time on the basis of the drive pulse selection data SI. After the drive pulse selection data SI of the register 20 is stored in the latch circuit 21, print information is input to the register 20 and the data stored in the latch circuit 21 is sequentially updated at the time of ejecting ink. Reference sign HGND in the drawing represents a ground terminal of the actuators 19 including a piezoelectric element. Even after the actuator 19 of a piezoelectric element is disconnected from the drive signal COM (drive pulses PCOM) by the selection switch 23 (after the selection switch 23 is turned off), the input voltage of the corresponding actuator 19 is maintained at the voltage just before the disconnection. That is, the actuators 19 including a piezoelectric element are capacitive loads.

Figure 6:
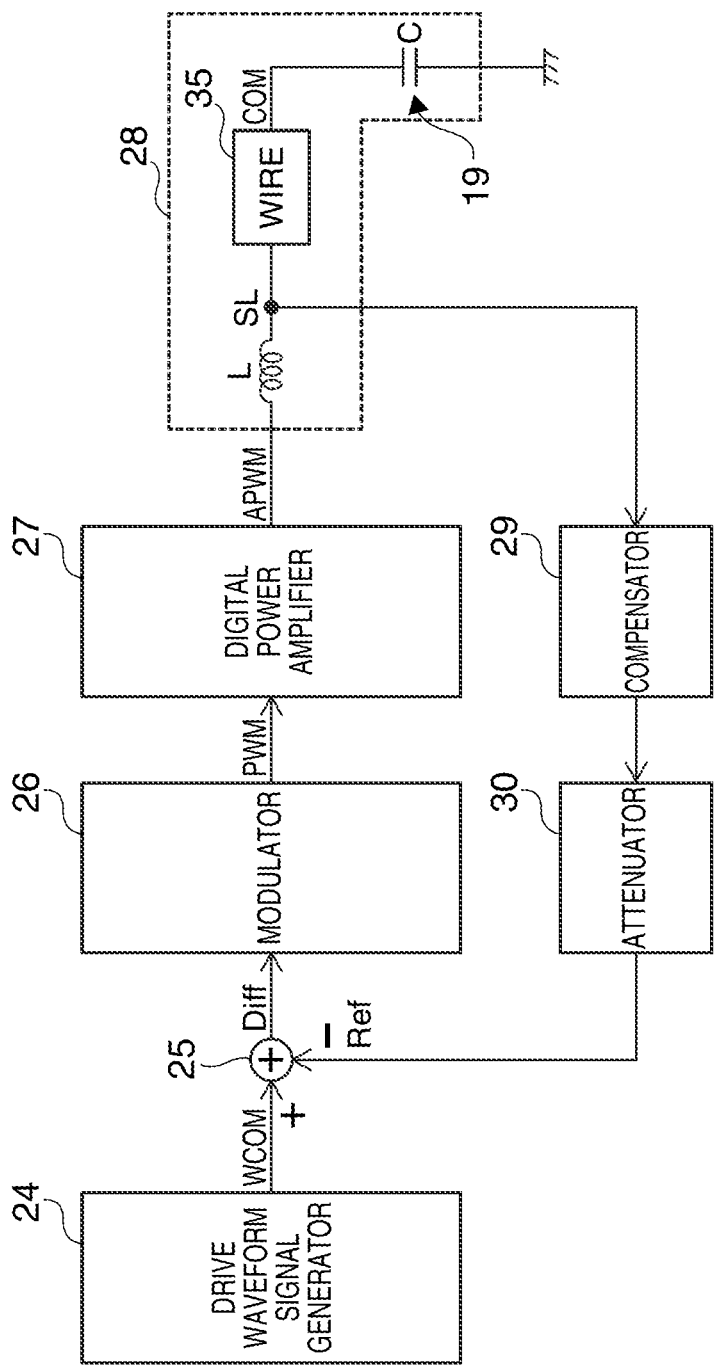
FIG. 6 is a block diagram illustrating a driver of an actuator.

FIG. 6 schematically shows the configuration of a driving circuit of the actuators 19. The driving circuit of the actuators is constructed in the head driver 16 of the control unit 11. In this embodiment, the driving circuit includes a drive waveform signal generator 24, a subtractor 25, a modulator 26, a digital power amplifier 27, and a smoothing filter 28. A compensator 29 and an attenuator 30 are inserted into a feedback circuit to the subtractor 25.

Here, the drive waveform signal generator 24 generates a drive waveform signal WCOM serving as a source of the drive signal COM (drive pulses PCOM), that is, a reference of a signal used to control the driving of the actuator 19, on the basis of drive waveform data DWCOM stored in advance. The subtractor 25 subtracts a feedback signal Ref from the drive waveform signal WCOM generated by the drive waveform signal generator 24 and outputs a differential signal Diff. The modulator 26 pulse-modulates the differential signal Diff output from the subtractor 25. The digital power amplifier 27 power-amplifies the modulated signal PWM modulated by the modulator 26. The smoothing filter 28 smoothes the power-amplified modulated signal APWM power-amplified by the digital power amplifier 27 and outputs the smoothed signal as a drive signal COM to the actuators 19 including a piezoelectric element.

The drive waveform signal generator 24 converts drive waveform data DWCOM including digital data into voltage signals and outputs the voltage signals after holding the resultant signals for a predetermined number of sampling periods. The subtractor 25 is an analog subtraction circuit into which a resistor for a proportional constant may be inserted.

Figure 7:
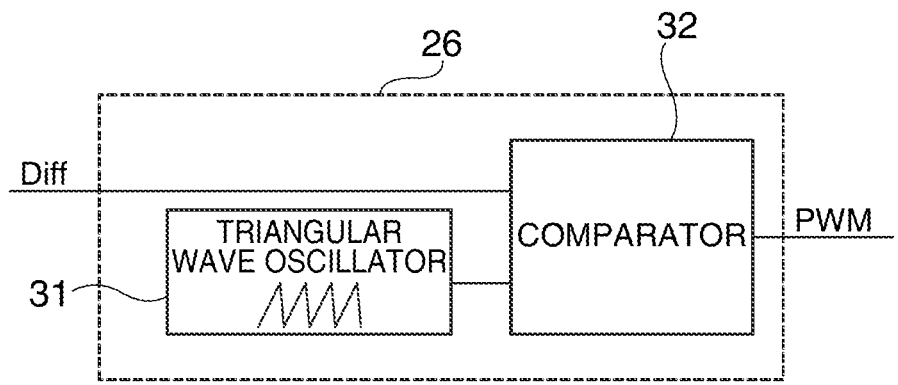
FIG. 7 is a block diagram illustrating a modulator shown in FIG. 6.

As shown in FIG. 7, the modulator 26 employs a pulse-width modulation (PWM) circuit. The pulse-width modulation circuit includes a triangular wave oscillator 31 outputting a triangular-wave signal of a predetermined frequency and a comparator 32 comparing the triangular-wave signal with the differential signal Diff and outputting a modulated signal PWM with a pulse duty which is in an ON-duty state, for example, when the differential signal Diff is greater than the triangular-wave signal. The modulator 26 may employ a pulse-modulation circuit such as a pulse density modulation (PDM) circuit. In this embodiment, the operating voltage range of the subtractor 25 employing the analog subtraction circuit is 0 to 5 V.

Figure 8:
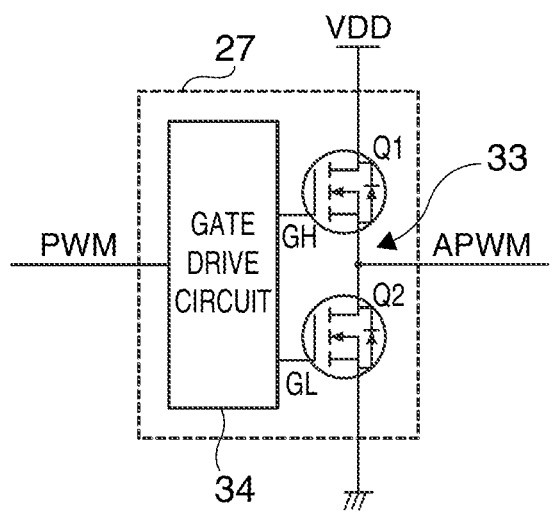
FIG. 8 is a block diagram illustrating a digital power amplifier shown in FIG. 6.

As shown in FIG. 8, the digital power amplifier 27 includes a half-bridge output terminal 33 including a high-side switching element Q1 and a low-side switching element Q2 so as to actually amplify power. The digital power amplifier 27 includes a gate drive circuit 34 adjusting gate-source signals GH and GL of the high-side switching element Q1 and the low-side switching element Q2 on the basis of the modulated signal PWM from the modulator 26. In the digital power amplifier 27, the gate-source signal GH of the high-side switching element Q1 is at a high level and the gate-source signal GL of the low-side switching element Q2 is at a low level when the modulated signal is at a high level. Accordingly, the high-side switching element Q1 is turned on and the low-side switching element Q2 is turned off. As a result, the output voltage Va of the half-bridge output terminal 33 is equal to a supply voltage VDD.

On the other hand, when the modulated signal is at a low level, the gate-source signal GH of the high-side switching element Q1 becomes the low level and the gate-source signal GL of the low-side switching element Q2 becomes the high level. Accordingly, the high-side switching element Q1 is turned off and the low-side switching element Q2 is turned on. As a result, the output voltage Va of the half-bridge output terminal 33 becomes 0.

When the high-side switching element Q1 and the low-side switching element Q2 are digitally driven in this way, a current flows in the turned-on switching element, but the drain-source resistance is very small and thus loss is almost zero. Since no current flows in the turned-off switching element, the loss is not generated. Therefore, the loss itself of the digital power amplifier 27 is very small and the digital power amplifier 27 can employ a switching element such as a small-sized MOSFET.

As shown in FIG. 6, the smoothing filter 28 includes an inductor L, an actuator 19 including a piezoelectric element as a capacitive load, and a wire 35 to form a secondary low-pass filter. In this embodiment, since plural ink jet heads 2 including the actuator 19 are disposed for the single control unit 11 and are separated from each other, the wire 35 including board interconnections is necessary between the control unit 11 and the ink jet heads 2. Since the wire 35 generally has a resistance component and an inductance component, the smoothing filter 28 according to this embodiment constitutes a secondary low-pass filter including the inductance component of the inductor L, the resistance component and the inductance component of the wire 35, and the capacitance component of the actuator 19. The signal amplitude of the modulation frequency, that is, the pulse-modulation frequency, generated in the modulator 26 is attenuated and removed by the smoothing filter 28 and the drive signal COM (drive pulses PCOM) is output to the actuator 19.

Figure 9A:
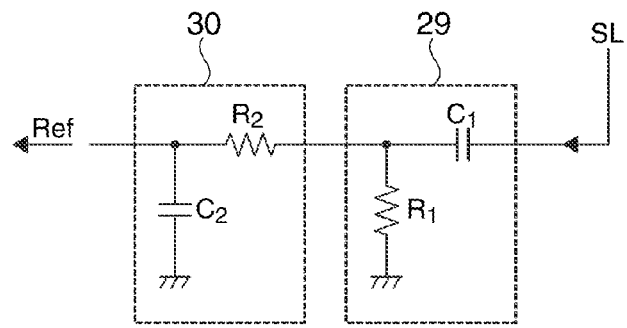
FIGS. 9A and 9B are diagrams illustrating a feedback circuit shown in FIG. 6, where

The final or output drive signal is ideally fed back as the feedback signal. However, when the wire 35 is necessary between the control unit 11 and the actuator 19 as in this embodiment, individual wires are necessary for feeding back the drive signal COM (drive pulses PCOM) from the actuator 19, which is not realistic. Therefore, in this embodiment, an inductor output signal SL is extracted from the connecting point between the inductor L of the smoothing filter 28 and the wire 35 and is fed back to the feedback circuit. As described above, the compensator 29 and the attenuator 30 are inserted into the feedback circuit. In this embodiment, as shown in FIG. 9A, a primary high-pass filter including a capacitor $C_1$ and a resistor $R_1$ is employed as the compensator 29, and a primary low-pass filter including a resistor $R_2$ and a capacitor $C_2$ is employed as the attenuator 30. As known widely, the high-pass filter has a phase-preceding or phase-shifting characteristic and thus can compensate for the feedback signal by causing the phase of the feedback signal Ref to precede the phase of the input using this characteristic. The phase-preceding or phase-shifting characteristic is also referred to as a differential characteristic. On the other hand, the low-pass filter has a phase-lag characteristic. The phase-lag characteristic is also referred to as an integral characteristic.

Figure 9B:
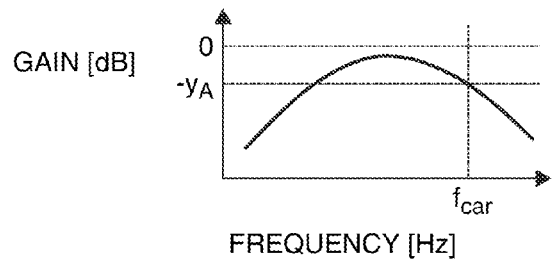

The feedback circuit including the combination of the compensator 29 employing the high-pass filter and the attenuator 30 employing the low-pass filter has the frequency characteristic shown in FIG. 9B. Particularly, a predetermined negative gain $-y_A$ is obtained in the modulation frequency or the modulation frequency band $f_{car}$ by the attenuator 30.

Figure 10:
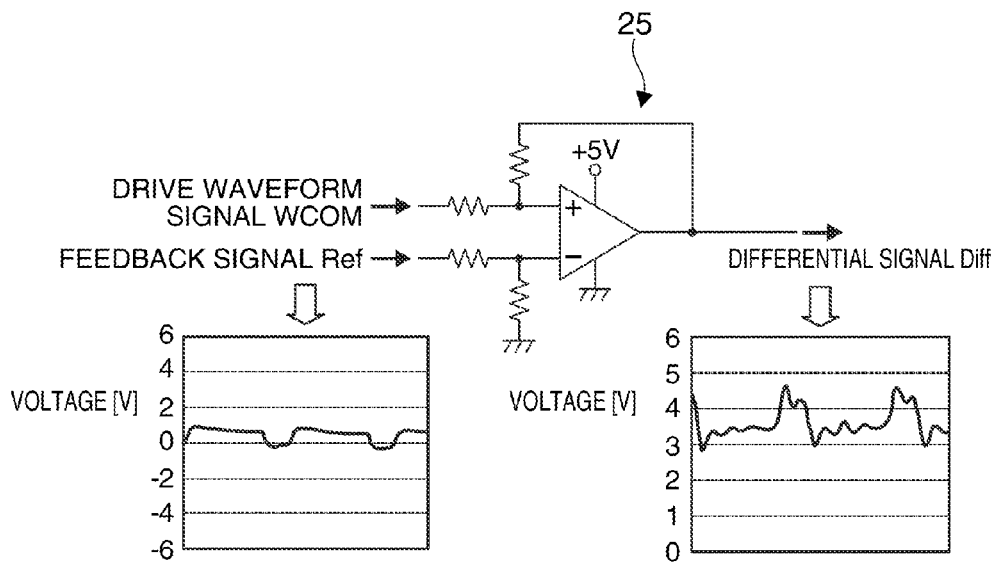
FIG. 10 is a diagram illustrating input and output signals of a subtractor shown in FIG. 6.

FIG. 10 shows an example of the feedback signal Ref input to the subtractor 25 and the differential signal Diff output from the subtractor 25 (a typical drive waveform signal, not the drive waveform signal including the above-mentioned trapezoidal voltage signal, is shown in the drawing). As can be clearly seen from the drawing, the signal amplitude of a high frequency corresponding to the modulation frequency or the modulation frequency band $f_{car}$ of the feedback signal Ref is attenuated well. As a result, the differential signal Diff does not exceed the operating voltage range of 0 to 5 V of the subtractor 25. In this way, when the differential signal Diff does not exceed the operating voltage range of the subtractor 25, it does not exceed the operating voltage range of the modulator 26 and thus the power-amplified modulated signal APWM which is the output signal of the digital power amplifier 27 and the drive signal COM (drive waveform signal PCOM) applied to the actuator 19 are also corrected. The compensation using the feedback circuit is established.

Figure 11:
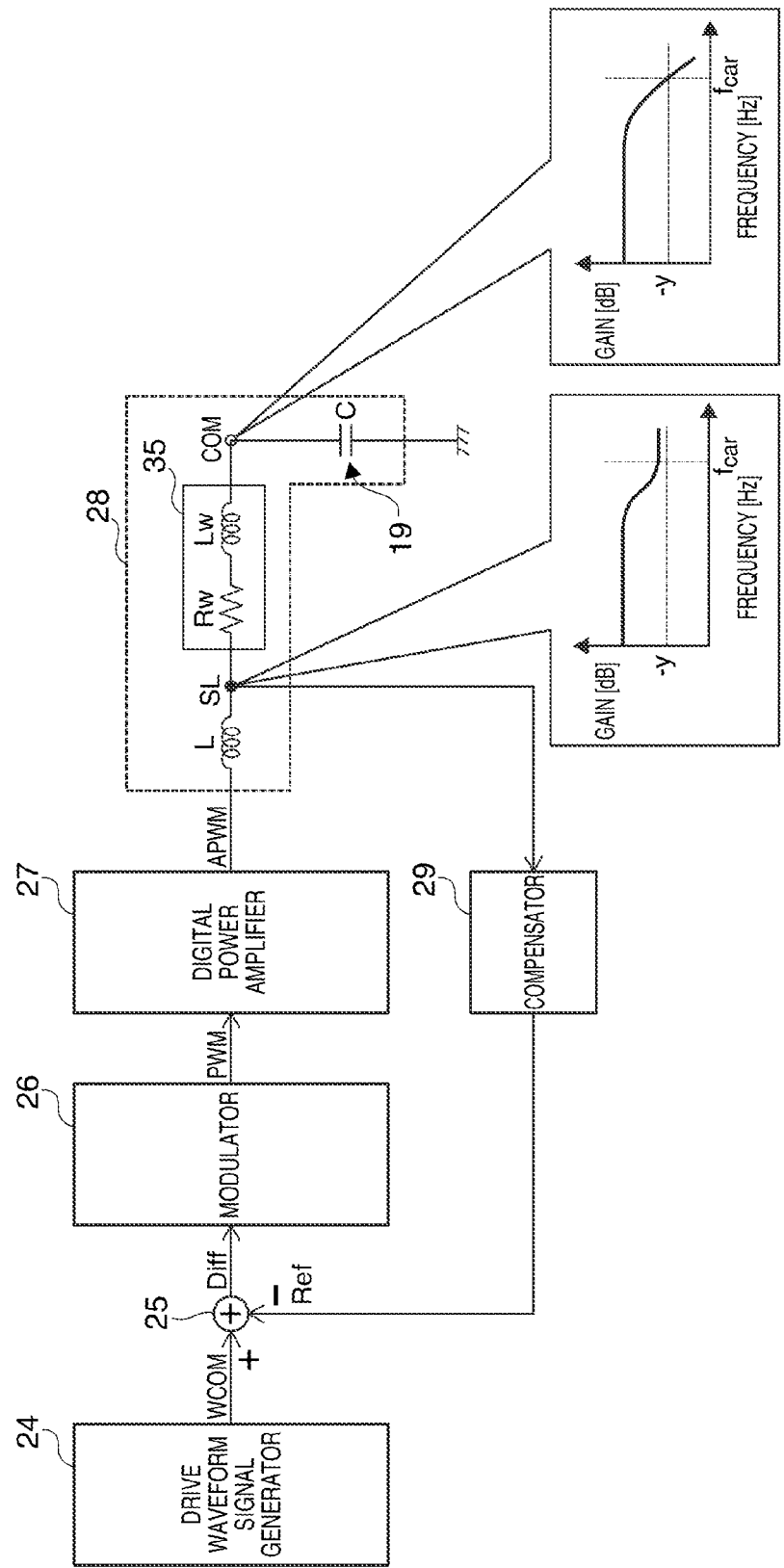
FIG. 11 is a block diagram illustrating a driver of an actuator and a feedback circuit according to the related art.

FIG. 11 shows an example of a drive circuit and a feedback circuit according to the related art in which only the compensator 29 is inserted in to the feedback circuit, as described in JP-A-2007-96364. When a secondary low-pass filter including the inductance component of an inductor and the capacitance component of a capacitor is necessary as the smoothing filter 28, it is ideal in consideration of the stability of a system that the capacitor on the output side of the inductor L in the drawing is grounded and a dumping resistor is inserted before and after the inductor. However, when the capacitor is grounded or the dumping resistor is inserted, the power consumption increases. Therefore, the dumping resistor can be made to be unnecessary by feeding back the output signal using the capacitance component C of the actuator 19 instead of the capacitor. In this case, the driving circuit and the feedback circuit shown in FIG. 11 can be considered.

Since the drive signal COM (drive pulses PCOM) applied to the actuator 19 is important in the smoothing filter 28, it is designed that the frequency characteristic in the connecting point between the actuator 19 and the wire 35 should be a predetermined negative gain $-y$ in the modulation frequency or the modulation frequency band $f_{car}$. However, the function of the smoothing filter 28 is not satisfactorily exhibited in the connecting point between the inductor L of the smoothing filter 28 and the wire 35 and the predetermined negative gain $-y$ is not obtained in the modulation frequency or the modulation frequency band $f_{car}$. Accordingly, the signal amplitude of the modulation frequency or the modulation frequency band $f_{car}$ may remain in the inductor output signal SL.

Figure 12A:
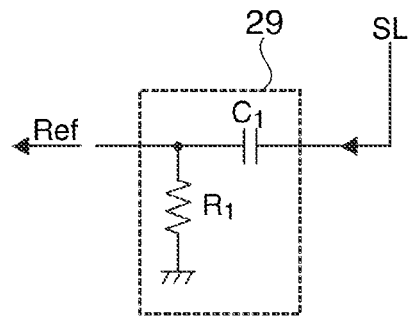
FIGS. 12A and 12B are diagrams illustrating a feedback circuit shown in FIG. 11, where
Figure 12B:
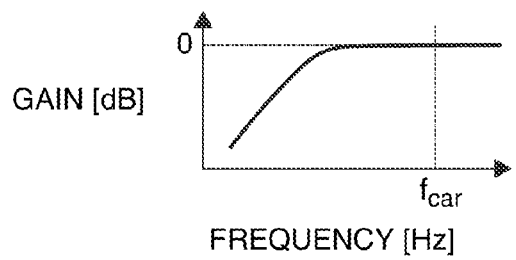
Figure 13:
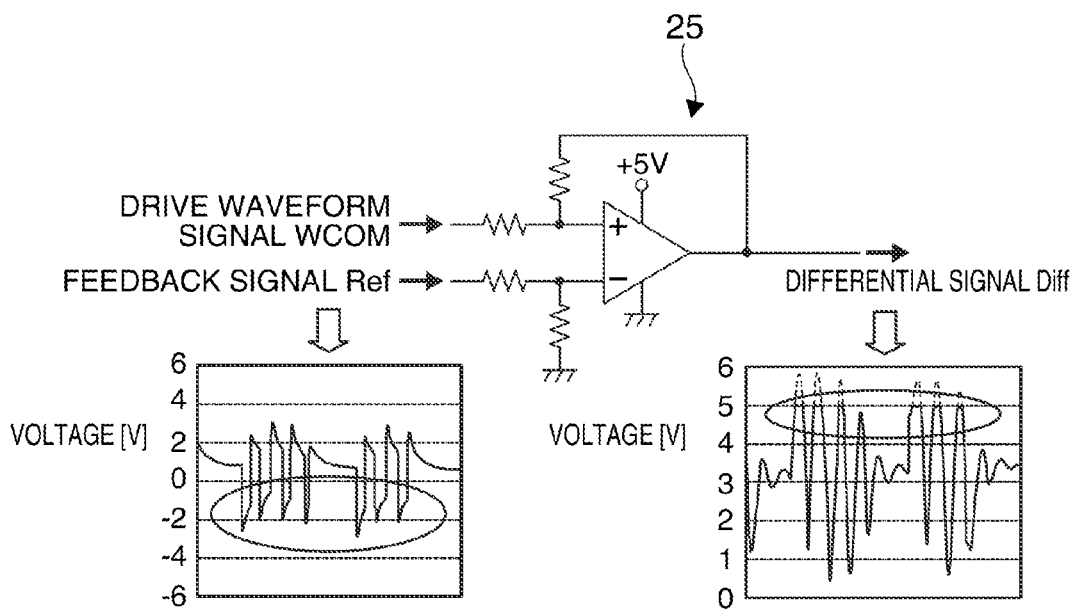
FIG. 13 is a diagram illustrating input and output signals of a subtractor shown in FIG. 11.

FIG. 12A shows the feedback circuit of FIG. 11. Similarly to FIGS. 9A and 9B, when the compensator 29 is a primary high-pass filter including a capacitor $C_1$ and a resistor $R_1$, the frequency characteristic (which is the same as the frequency characteristic of the compensator 29 in this case) of the feedback circuit is that the gain in the modulation frequency or the modulation frequency band $f_{car}$ is 0, that is, is not attenuated at all. Accordingly, the signal amplitude of the modulation frequency or the modulation frequency band $f_{car}$ remains in the feedback signal Ref. For example, as shown in FIG. 13, when the signal amplitude modulation frequency or the modulation frequency band $f_{car}$ remains in the feedback signal Ref, the differential signal Diff output from the subtractor 25 exceeds the operating voltage range of 0 to 5 V of the subtractor 25 and the differential signal Diff which should be inherently indicated by the two-dot chained line is cut off by the upper limit 5V of the operating voltage as indicated by the solid line and is thus distorted. In this way, when the differential signal Diff is distorted, the modulated signal PWM and the power-amplified modulated signal APWM are also distorted and the drive signal COM (drive pulses PCOM) is thus distorted. Thus, the compensation by the feedback circuit is not established.

On the contrary, in the feedback circuit according to this embodiment, the compensation can be established by the combination of the compensator 29 causing the phase to precede or shift and the attenuator 30 attenuating the signal amplitude of the modulation frequency or the modulation frequency band $f_{car}$ and the precision of the drive signal COM (drive pulses PCOM) can be guaranteed. As described above, the high-pass filter has a phase-preceding characteristic and the low-pass filter has a phase-lag characteristic. When the high-pass filter is employed as the compensator 29 and the low-pass filter is employed as the attenuator 30, it is possible to set both transfer characteristics by setting constants and thus to finely adjust the frequency characteristic.

Figure 14A:
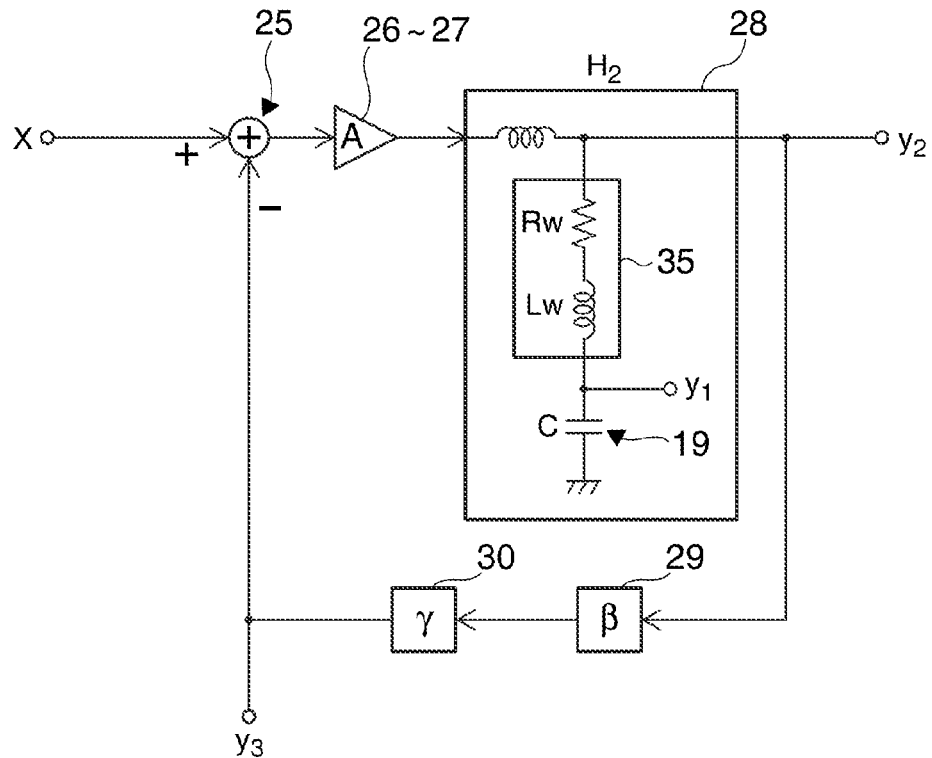
FIGS. 14A and 14B are diagrams illustrating an equivalent circuit of the driver of the actuator shown in FIG. 6.
Figure 14B:
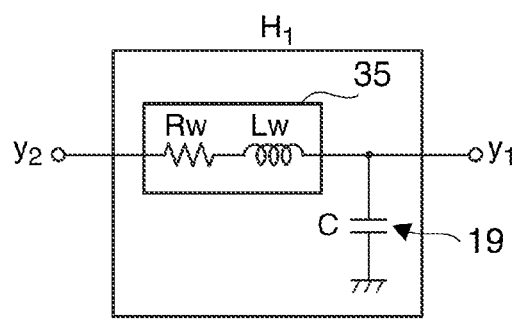

FIG. 14A shows an equivalent circuit of the actuator driving circuit shown in FIG. 6. In FIG. 14A, an input signal x corresponds to the drive waveform signal WCOM and the output signal $y_1$ corresponds to the drive signal COM (drive pulses PCOM). An output signal $y_2$ corresponds to the inductor output signal SL and an output signal $y_3$ corresponds to the feedback signal Ref. It is assumed that the transfer function of the smoothing filter 28 is $H_2$, the gain from the modulator 26 to the digital power amplifier 27 is A, the transfer function of the compensator 29 is β, and the transfer function of the attenuator 30 is γ. FIG. 14B shows an equivalent circuit of from the wire 35 to the actuator 19, where the transfer function of the equivalent circuit is $H_1$.

When the output signal $y_1$ in response to the input signal x, that is, the transfer function of the drive signal COM (drive pulses PCOM), is $Gy_1$ and the output signal $y_2$ in response to the input signal x, that is, the transfer function of the inductor output signal SL, is $Gy_2$, Expression (3) can be obtained from Expressions (1) and (2).

$$y_1 = H_1 \cdot y_2 = H_1 \cdot G_{y2} \cdot x \quad (1)$$

$$G_{y1} = \frac{y_1}{x} = H_1 \cdot G_{y2} \quad (2)$$

$$\Downarrow$$

$$G_{y1} = \frac{1}{\frac{\gamma \cdot \beta}{H_1} + \frac{1}{A \cdot H_1 \cdot H_2}} \quad (3)$$

Since the output signal $y_2$ and the output signal $y_3$ have the relationship of Expression (4), Expression (5) can be obtained by expressing the output signal $y_2$ by the transfer function $Gy_2$, and the output signal $y_3$ in response to the input signal x, that is, the transfer function $Gy_3$ of the feedback signal Ref, is expressed by Expression (6).

$$y_3 = \gamma \cdot \beta \cdot y_2 \quad (4)$$

$$y_3 = \gamma \cdot \beta \cdot (G_{y2} \cdot x) \quad (5)$$

$$\Downarrow$$

$$G_{y3} = \frac{y_3}{x} = \gamma \cdot \beta \cdot G_{y2} \quad (6)$$

Regarding the output signal $y_2$, Expression (8) can be obtained from Expression (7). As a result, the transfer function $Gy_2$ of the output signal $y_2$ in response to the input signal x is expressed by Expression (9).

$$y_2 = A \cdot H_2 \cdot (x - \gamma \cdot \beta \cdot y_2) \quad (7)$$

$$y_2 = \frac{1}{\gamma \cdot \beta + \frac{1}{A \cdot H_2}} \cdot x \quad (8)$$

$$\Downarrow$$

$$G_{y2} = \frac{y_2}{x} = \frac{1}{\gamma \cdot \beta + \frac{1}{A \cdot H_2}} \quad (9)$$

Figure 15:
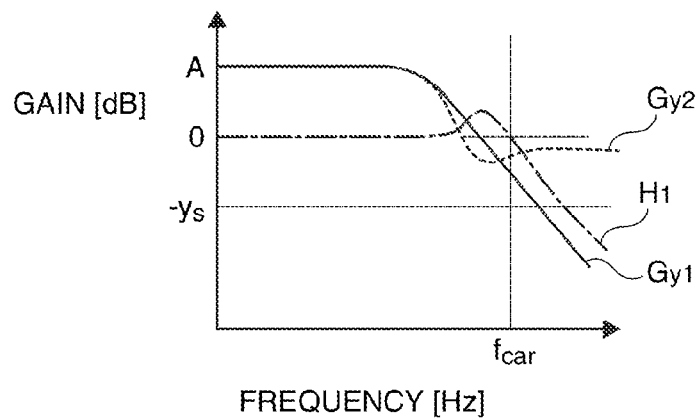
FIG. 15 is a diagram illustrating a frequency characteristic of the circuit shown in FIGS. 14A and 14B.

FIG. 15 shows an example of the output signal $y_1$ in response to the input signal x, that is, transfer function $Gy_1$ of the drive signal COM (drive pulses PCOM), and the transfer function $H_1$ from the wire 35 to the actuator 19. The transfer function $Gy_1$ is a target value and also a designed value. On the other hand, the transfer function $H_1$ is a predetermined value. Accordingly, the output signal $y_2$ in response to the input signal x, that is, the transfer function $Gy_2$ of the inductor output signal SL, is the same as indicated by the broken line in the drawing.

Figure 16A:
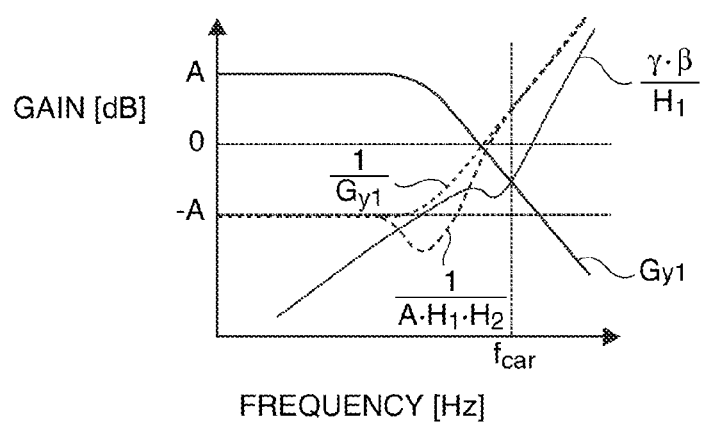
FIGS. 16A and 16B are diagrams illustrating a frequency characteristic of the circuit shown in FIGS. 14A and 14B.

As described above, the feedback from the smoothing filter 28 employing the secondary low-pass filter is performed to remove the resonance peak from the characteristic of the output signal $y_1$ in response to the input signal x, that is, the transfer function $Gy_1$ of the drive signal COM (drive pulses PCOM). Accordingly, the transfer characteristic (gain) β of the compensator 29 is set to remove the resonance peak from the characteristic of the transfer function $Gy_1$. In this case, the transfer characteristic (gain) γ of the attenuator 30 can be first set to 1. For example, in order to remove the resonance peak from the transfer function $Gy_1$ expressed by Expression (3), the transfer characteristic (gain) γ of the compensator 29 is set by adding γ·β/$H_1$ to the transfer function of the reciprocal of A·$H_1$·$H_2$ having the resonance characteristic to cancel the resonance peak of 1/$Gy_1$, as shown in FIG. 16A.

Since the modulation frequency component is generated from the output of the digital power amplifier, the amount of attenuated amplitude of the modulation frequency Component is considered with reference to the output of the digital power amplifier. For example, in FIG. 16B, the gain of the modulation frequency component as viewed from the input x is the output A (dB) of the digital power amplifier and the gain of the modulation frequency component after the attenuator 30 as viewed from the input x is $-y_s$ (dB). That is, the gain of the modulation frequency component varies from A (dB) to $-y_s$ (dB) and the amount of attenuated amplitude of the modulation frequency or the modulation frequency band $f_{car}$ is $A+y_s$ (dB).

Figure 16B:
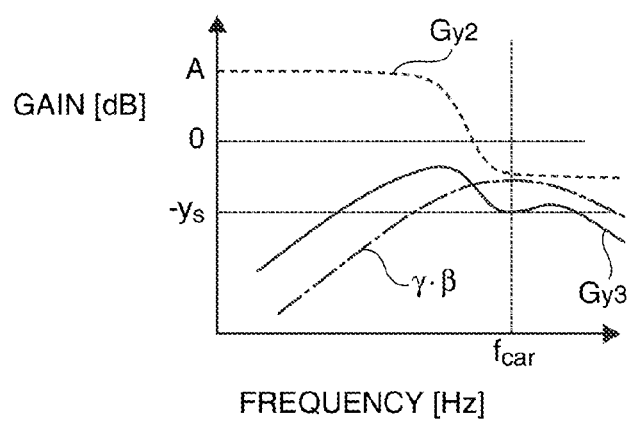

As shown in FIG. 16B, the amount of attenuated amplitude $A+y_s$ (dB) of the modulation frequency or the modulation frequency band $f_{car}$ in the feedback signal Ref is set so as not to exceed the operating voltage range (the range of 0 to 5 V in this embodiment) of a so-called analog signal system such as the subtractor 25 or the modulator 26. The transfer characteristic (gain) γ of the attenuator 30 is set so that the amount of attenuated signal amplitude of the modulation frequency or the modulation frequency band $f_{car}$ in the output signal $y_3$ in response to the input signal x, that is, the transfer function $Gy_3$ of the feedback signal Ref, is equal to or less than $A+y_s$ (dB). At this time, since the characteristic of the transfer function $Gy_1$ of the drive signal COM (drive pulses PCOM) does not have to be greatly changed, the adjustment of the transfer function $Gy_3$ of the feedback signal Ref due to the transfer characteristic (gain) γ of the attenuator 30 verifies the characteristic variation of the transfer function $Gy_1$ of the drive signal COM (drive pulses PCOM).

In the capacitive load driving circuit and the ink jet printer according to this embodiment, when the drive signal COM (drive pulses PCOM) is applied to the actuator 19 employing a capacitive load, the volume of the pressure chamber of each ink jet head 2 is reduced to eject ink in the pressure chamber. When a printing operation is performed on the printing medium 1 using the ejected ink, the inductor L is connected to the actuator 19 employing a capacitive load with the wire 35 to constitute the smoothing filter 28, and the inductor output signal SL output from the connecting point between the inductor L and the wire 35 is made to pass through the compensator 29 and the attenuator 30 and is then used as the feedback signal Ref to the subtractor 25. Accordingly, it is possible to attenuate the signal amplitude of the modulation frequency band $f_{car}$ in the feedback signal Ref by the use of the attenuator 30 while removing the resonance peak from the transfer function characteristic of the drive signal. As a result, it is possible to prevent the signal amplitude of the modulation frequency band $f_{car}$ exceeding the operating range of the subtractor 25 or the modulator 26 from remaining in the feedback signal Ref while compensating for the waveform of the drive signal and thus guarantee the precision of the drive signal, thereby performing a printing operation with high precision.

By setting the attenuator 30 to attenuate the feedback signal Ref so that the signal amplitude does not exceed the operating voltage range of at least one of the subtractor 25 and the modulator 26, it is possible to satisfactorily prevent the signal amplitude of the modulation frequency band $f_{car}$ exceeding the operating voltage range of the subtractor 25 or the modulator 26 from remaining in the feedback signal Ref.

By employing the attenuator 30 having a phase-lag characteristic, it is possible to remove the distortion of the feedback signal Ref by the use of the integrating function of the phase-lag characteristic. By adjusting the phase-lag characteristic of the attenuator 30 to adjust the frequency characteristic of the feedback circuit, it is possible to adjust the frequency characteristic of the drive signal COM (drive pulses PCOM).

Although it has been described in detail in the above-mentioned embodiment that the capacitive load driving circuit according to the invention is applied to a line head type ink jet printer, the capacitive load driving circuit according to the invention may be similarly applied to a multi-pass type ink jet printer.

A capacitive load driving circuit according to a second embodiment of the invention will be described below. In this embodiment, the same elements as described in the first embodiment are referenced by the same reference numerals and signs as described in the first embodiment and detailed description thereof will not be repeated.

Figure 17A:
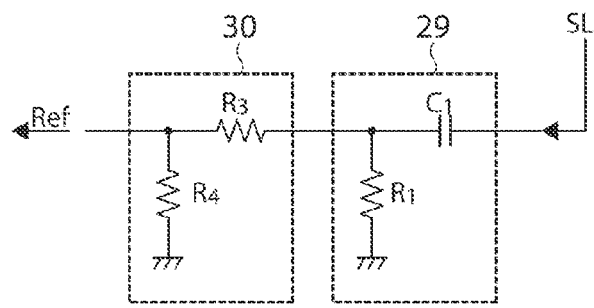
FIGS. 17A and 17B are diagrams illustrating an example of a feedback circuit disposed in the actuator driver show in FIG.

This embodiment is different from the first embodiment in the configuration of the feedback circuit disposed in the actuator driving circuit. Similarly to the first embodiment, the feedback circuit includes the compensator 29 and the attenuator 30, but the specific configuration thereof is changed. FIG. 17A is a block diagram illustrating an example of the compensator 29 and the attenuator 30 disposed in the feedback circuit according to this embodiment. Similar to the compensator of the first embodiment, the compensator 29 shown in this example employs a primary high-pass filter including a capacitor $C_1$ and a resistor $R_1$, but the attenuator 30 employs a voltage divider including a resistor $R_3$ inserted into the circuit and a resistor $R_4$ grounded on the output side thereof.

Figure 17B:
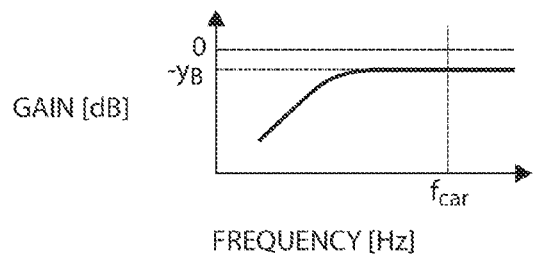

Accordingly, the frequency characteristic of the feedback circuit shown in FIG. 17A can be illustrated as shown in FIG. 17B. In this embodiment, it is possible to obtain a predetermined negative gain $-y_B$ in the modulation frequency or the modulation frequency band $f_{car}$ with the simple configuration of the combination of two resistors, thereby providing the attenuation in the modulation frequency band.

Figure 18A:
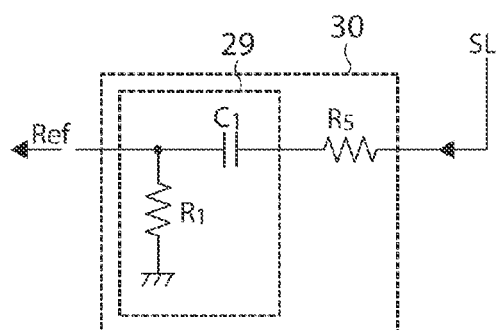
FIGS. 18A and 18B are diagrams illustrating another example of the feedback circuit disposed in the actuator driver shown in FIG. 3, where
Figure 18B:
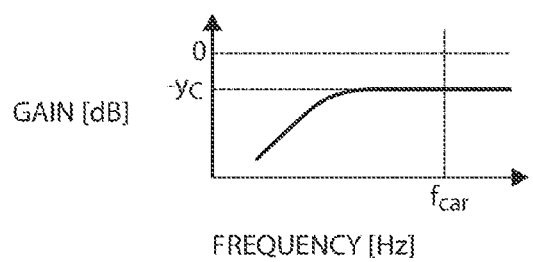

FIG. 18A is a block diagram illustrating another example of the compensator 29 and the attenuator 30 disposed in the feedback circuit according to this embodiment. Similar to the compensator of the first embodiment, the compensator 29 shown in this example employs a primary high-pass filter including a capacitor $C_1$ and a resistor $R_1$. The attenuator 30 employs a voltage divider including a resistor $R_5$ inserted into the circuit and a grounded resistor $R_1$ in the compensator 29. That is, the attenuator 30 is constructed in combination with the compensator 29. The frequency characteristic of the feedback circuit shown in FIG. 18A can be illustrated as shown in FIG. 18B. In this embodiment, similar to the FIGS. 17A and 17B, it is possible to obtain a predetermined negative gain $-y_c$ in the modulation frequency or the modulation frequency band $f_{car}$ with the simple configuration of the combination of two resistors, thereby providing the attenuation in the modulation frequency band and/or reducing the number of resistors used. In the actuator driving circuit according to this embodiment, it is possible to simplify the feedback circuit.

Figure 19:
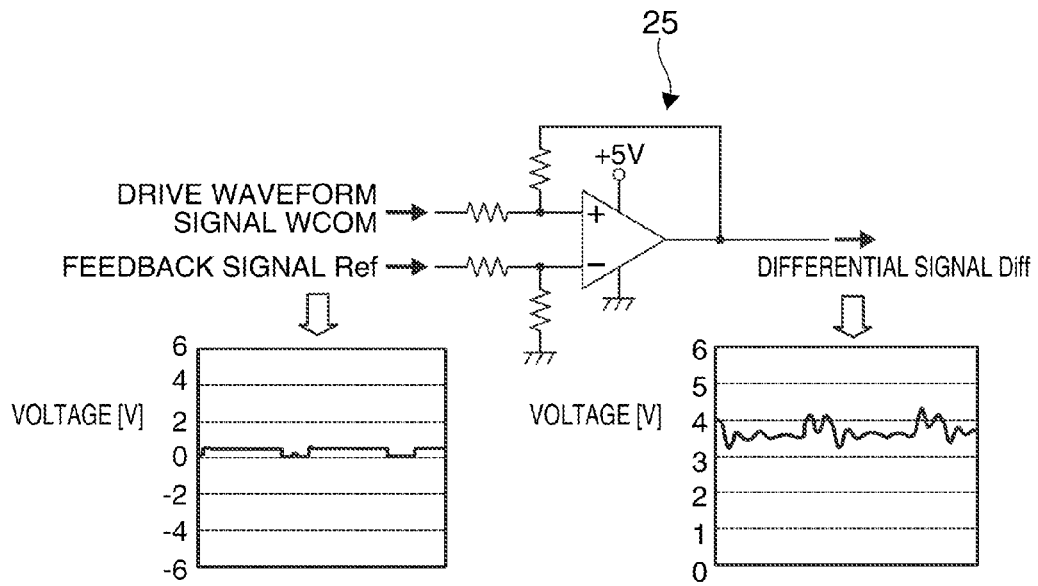
FIG. 19 is a diagram illustrating input and output signals of the subtractor disposed in the actuator driver shown in FIG. 3.

FIG. 19 shows an example of the feedback signal Ref input to the subtractor 25 and the differential signal Diff output from the subtractor 25 according to this embodiment (a typical drive waveform signal, not the drive waveform signal including the above-mentioned trapezoidal voltage signal, is shown in the drawing). As can be clearly seen from the drawing, the signal amplitude of a high frequency corresponding to the modulation frequency or the modulation frequency band $f_{car}$ of the feedback signal Ref is attenuated well. As a result, the differential signal Diff does not exceed the operating voltage range of 0 to 5 V of the subtractor 25. In this way, when the differential signal Diff does not exceed the operating voltage range of the subtractor 25, it does not exceed the operating voltage range of the modulator 26. Thus the power-amplified modulated signal APWM, which is the output signal of the digital power amplifier 27, and the drive signal COM (drive waveform signal PCOM) applied to the actuator 19 are also corrected. In this manner, the compensation using the feedback circuit is established.

In this way, even when the capacitive load driving circuit according to this embodiment is used, it is possible to attenuate the signal amplitude of the high frequency corresponding to the modulation frequency or the modulation frequency band $f_{car}$ of the feedback signal Ref while removing the resonance peak from the transfer function characteristic of the drive signal. As a result, since the differential signal Diff does not exceed the operating voltage range of 0 to 5 V of the subtractor 25, it is possible to establish the compensation using the feedback circuit. Since the attenuator includes one or more resistors, it is possible to remove the distortion of the feedback signal Ref with a simpler configuration.

A capacitive load driving circuit according to a third embodiment of the invention will be described below. In this embodiment, the same elements as described in the first embodiment are referenced by the same reference numerals and signs as described in the first embodiment and detailed description thereof will not be repeated.

This embodiment is different from the first and second embodiments in the configuration of the feedback circuit disposed in the actuator driving circuit. Similarly to the first and second embodiments, the feedback circuit includes the compensator 29 and the attenuator 30, but the specific configuration thereof is changed.

Figure 20A:
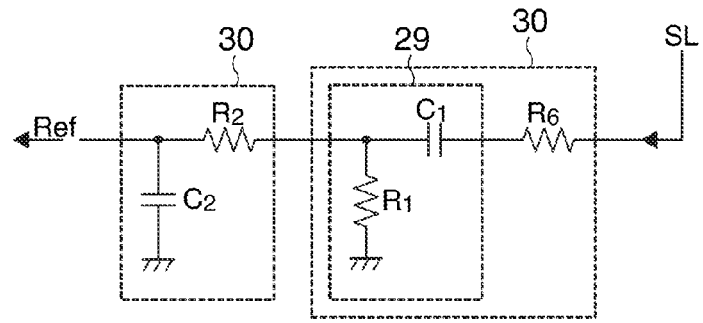
FIGS. 20A and 20B are diagrams illustrating the feedback circuit disposed in the actuator driver shown in FIG. 3, where
Figure 20B:
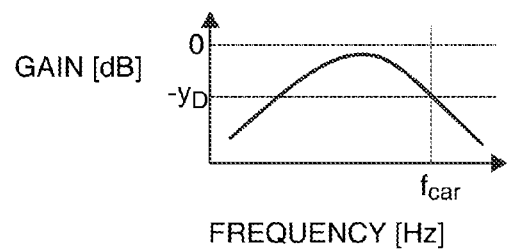

FIG. 20A is a block diagram illustrating an example of the compensator 29 and the attenuator 30 disposed in the feedback circuit according to this embodiment. Similar to the compensator and the attenuator of the first embodiment, the compensator 29 and the attenuator 30 shown in the drawing employ a primary high-pass filter including a capacitor $C_1$ and a resistor $R_1$ and a primary low-pass filter including a resistor $R_2$ and a capacitor $C_2$, respectively. In this embodiment, a resistor $R_6$ is inserted into the input side of the high-pass filter constituting the compensator 29 to constitute the attenuator 30 employing a voltage divider including the resistor $R_6$ and the grounded resistor $R_1$ of the compensator 29. Accordingly, the frequency characteristic of the feedback circuit shown in FIG. 20A can be illustrated as shown in FIG. 20B and it is thus possible to further reduce the gain in the modulation frequency or the modulation frequency band $f_{car}$ into a predetermined negative gain $-y_D$, compared with the feedback circuit according to the first embodiment shown in FIGS. 9A and 9B. In the actuator driving circuit according to this embodiment, it is possible to variously set the attenuation characteristic of the attenuator 30.

Figure 21:
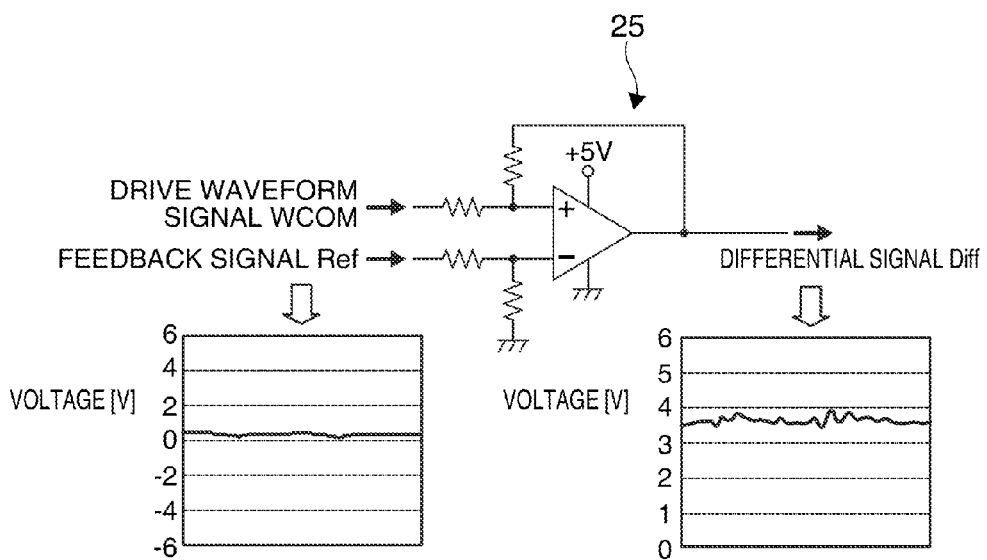
FIG. 21 is a diagram illustrating input and output signals of the subtractor disposed in the actuator driver shown in FIG. 3.

FIG. 21 shows an example of the feedback signal Ref input to the subtractor 25 and the differential signal Diff output from the subtractor 25 according to this embodiment (a typical drive waveform signal, not the drive waveform signal including the above-mentioned trapezoidal voltage signal, is shown in the drawing). As can be clearly seen from the drawing, the signal amplitude of a high frequency corresponding to the modulation frequency or the modulation frequency band $f_{car}$ of the feedback signal Ref is attenuated well. As a result, the differential signal Diff does not exceed the operating voltage range of 0 to 5 V of the subtractor 25. In this way, when the differential signal Diff does not exceed the operating voltage range of the subtractor 25, it does not exceed the operating voltage range of the modulator 26. Thus the power-amplified modulated signal APWM, which is the output signal of the digital power amplifier 27, and the drive signal COM (drive waveform signal PCOM) applied to the actuator 19 are also corrected well, whereby the compensation using the feedback circuit is established.

In this way, even when the capacitive load driving circuit according to this embodiment is used, it is possible to attenuate the signal amplitude of the high frequency corresponding to the modulation frequency or the modulation frequency band $f_{car}$ of the feedback signal Ref while removing the resonance peak from the transfer function characteristic of the drive signal. As a result, since the differential signal Diff does not exceed the operating voltage range of 0 to 5 V of the subtractor 25, it is possible to establish the compensation using the feedback circuit and also to more greatly remove the distortion of the feedback signal Ref with plural attenuators.

In the above-mentioned embodiment, it has been described in detail that the capacitive load driving circuit according to the invention is applied to the driving of actuators which are capacitive loads of an ink jet printer. However, the capacitive load driving circuit according to the invention may be similarly applied to the driving of a capacitive load used in a fluid ejecting apparatus. Examples of the fluid ejecting apparatus employing a capacitive load include a water pulse scalpel suitably installed in a distal end of a catheter which is inserted into a blood vessel to remove blood clots and the like and a water pulse scalpel suitable for incising or excising a biological tissue. The fluid used as the water pulse scalpel is water or physiological saline.

The water pulse scalpel ejects a high-pressure liquid supplied from a pump as a pulse flow. At the time of ejecting a pulse flow, a piezoelectric element as a capacitive load is driven to displace a diaphragm constituting a fluid chamber to generate the pulse flow. In the water pulse scalpel, the piezoelectric element as a capacitive load and a fluid ejection controller controlling the piezoelectric element are disposed separately from each other. Accordingly, by applying the capacitive load driving circuit according to the invention to the water pulse scalpel, it is possible to guarantee the precision of the drive signal of the capacitive load, thereby ejecting a fluid with high precision.

The fluid ejecting apparatus employing the capacitive load driving circuit according to the invention may be embodied as a fluid ejecting apparatus ejecting a liquid (including a liquid-like material in which functional material particles are dispersed and a fluidic material such as gel in addition to the liquid) other than the ink or the physiological saline or a fluid (including a solid which can be ejected as a fluid) other than the liquid. Examples thereof include a liquid-like material ejecting apparatus ejecting a liquid-like material with dispersed or melted electrode materials or color materials which are used to produce, for example, a liquid crystal display, an EL (Electroluminescence) display, a surface emission display, and a color filter, a fluid ejecting apparatus ejecting biological organic materials used to produce a bio chip, and a fluid ejecting apparatus which is used as a precision pipette ejecting a liquid as a sample. Examples thereof also include a fluid ejecting apparatus ejecting lubricant to precision machinery such as watches and cameras with a pinpoint and a fluid ejecting apparatus ejecting a transparent resin solution of an ultraviolet-curable resin or the like on a substrate so as to form micro semi-spherical lenses (optical lenses) used for optical communication devices. Examples thereof further include a fluid ejecting apparatus ejecting an etchant of acid or alkali so as to etch a substrate and the like, a fluidic material ejecting apparatus ejecting gel, and a fluid-ejecting recording apparatus ejecting a solid such as toner powders. The invention may be applied to any type of ejecting apparatus thereof.

What is claimed is:
1. A capacitive load driving circuit comprising:
   a drive waveform signal generator that generates a drive waveform signal;
   a subtractor that outputs a differential signal between the drive waveform signal and a feedback signal;
   a modulator that pulse-modulates the differential signal and outputs a modulated signal;

a digital power amplifier that amplifies the power of the modulated signal and outputs a power-amplified modulated signal;

a smoothing filter that is constructed by connecting an inductor and a capacitive load with a wire, smoothes the power-amplified modulated signal, and outputs a drive signal of the capacitive load; and a feedback circuit which outputs the feedback signal, wherein the feedback circuit comprises:

a first portion including a first resistance element and a capacitance element serially connected to the first resistance element; and a second portion including a second resistance element having a first terminal and a second terminal, wherein the first terminal is connected to a terminal of the first portion, and the second terminal is connected to a reference potential, wherein the first resistance element and the capacitance element of the first portion are located between a first connecting point where the inductor is connected to the wire and a second connecting point where the first terminal is connected to the terminal of the first portion, wherein a signal output from the first connecting point is made to pass through the feedback circuit and is then used as the feedback signal to the subtractor.

2. The capacitive load driving circuit according to claim 1, wherein the capacitance element is located between the first resistance element and the second connecting point.

3. The capacitive load driving circuit according to claim 1, wherein the second portion attenuates the signal amplitude so as not to exceed an allowable operating range of at least one of the subtractor and the modulator.

4. The capacitive load driving circuit according to claim 1, wherein the second portion has a phase-lag characteristic.

5. The capacitive load driving circuit according to claim 1, wherein the second portion includes one or more resistors.

6. The capacitive load driving circuit according to claim 1, wherein the second portion includes a plurality of attenuators.

7. An ink jet printer having a plurality of actuators as a capacitive load in an ink jet head, applying a drive signal to the actuators so as to reduce a volume of a pressure chamber and to eject ink in the pressure chamber, and performing a printing operation on a printing medium with the ejected ink, the ink jet printer comprising the capacitive load driving circuit according to claim 1, wherein said smoothing filter is adapted to output said drive signal.

8. A fluid ejecting apparatus having an actuator as a capacitive load connected to a diaphragm and applying a drive signal to the actuators so as to reduce a volume of a fluid chamber by means of the diaphragm and to eject fluid in the fluid chamber, the fluid ejecting apparatus comprising the capacitive load driving circuit according to claim 1, wherein said smoothing filter is adapted to output said drive signal.

* * * * *